United States Patent
Tateyama

(10) Patent No.: US 9,683,970 B2
(45) Date of Patent: Jun. 20, 2017

(54) OBJECT INFORMATION ACQUIRING APPARATUS AND CONTROL METHOD FOR THE OBJECT INFORMATION ACQUIRING APPARATUS

(71) Applicant: CANON KABUSHIKI KAISHA, Tokyo (JP)

(72) Inventor: Jiro Tateyama, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 417 days.

(21) Appl. No.: 14/197,345

(22) Filed: Mar. 5, 2014

(65) Prior Publication Data
US 2014/0260632 A1 Sep. 18, 2014

(30) Foreign Application Priority Data
Mar. 14, 2013 (JP) ................. 2013-051905

(51) Int. Cl.
*A61B 5/00* (2006.01)
*A61B 8/00* (2006.01)
(Continued)

(52) U.S. Cl.
CPC .......... *G01N 29/24* (2013.01); *A61B 5/0095* (2013.01); *A61B 8/40* (2013.01); *A61B 8/429* (2013.01);
(Continued)

(58) Field of Classification Search
CPC ............... G01N 29/24; G01N 29/032; G01N 2291/02433; A61B 5/0095; A61B 8/40; A61B 8/429; A61B 8/4461; A61B 5/0037
(Continued)

(56) References Cited

U.S. PATENT DOCUMENTS 7,661,293 B2 * 2/2010 Dam .................... G01N 29/032
73/19.03
7,726,174 B2 * 6/2010 Riley .................... A61M 5/365
73/19.03
(Continued)

FOREIGN PATENT DOCUMENTS

EP 2272435 * 1/2011
JP H02-104343 4/1990
(Continued)

OTHER PUBLICATIONS

JPO Office Action issued Jan. 17, 2017 in counterpart Japanese patent application 2013-051905, with translation.

*Primary Examiner* — J M Saint Surin
(74) *Attorney, Agent, or Firm* — Fitzpatrick, Cella, Harper & Scinto

(57) ABSTRACT

An object information acquiring apparatus that transmits an acoustic wave to an object, and receives and analyzes the reflected acoustic wave to acquire internal information of the object, comprises a probe that transmits and receives the acoustic wave; a holding member disposed between the object and the probe to hold the object; and an air bubble detection unit that detects an air bubble present between the object and the holding member on the basis of an intensity of the acoustic wave received after a first time from the transmission by the probe, the first time being calculated on the basis of a time when the acoustic wave reaches a predetermined distance.

20 Claims, 15 Drawing Sheets

(51) Int. Cl.
*G01N 29/032* (2006.01)
*G01N 29/24* (2006.01)

(52) U.S. Cl.
CPC .......... *G01N 29/032* (2013.01); *A61B 5/0037* (2013.01); *A61B 8/4461* (2013.01); *G01N 2291/02433* (2013.01)

(58) Field of Classification Search
USPC .......................................................... 73/632
See application file for complete search history.

(56) References Cited

U.S. PATENT DOCUMENTS

| | | |
|---|---|---|
| 2008/0045865 A1 | 2/2008 | Kislev ................................ 601/3 |
| 2008/0242997 A1* | 10/2008 | Lynch .................... G01N 29/07 |
| | | 600/455 |
| 2011/0230750 A1 | 9/2011 | Tateyama ...................... 600/407 |
| 2012/0022373 A1 | 1/2012 | Tateyama ...................... 600/437 |
| 2012/0238859 A1 | 9/2012 | Tokita et al. ................. 600/407 |
| 2014/0051969 A1 | 2/2014 | Suzuki .......................... 600/407 |

FOREIGN PATENT DOCUMENTS

| | | | | |
|---|---|---|---|---|
| JP | H04-033652 | | 2/1992 | |
| JP | 6074865 | * | 3/1994 | ............ G01M 11/00 |
| JP | 2008-519642 | | 6/2008 | |
| JP | 2011-156208 | | 8/2011 | |
| JP | 2012-231979 | | 11/2012 | |
| SU | 1157352 | * | 5/1985 | ............... G01C 9/06 |

\* cited by examiner

OBJECT INFORMATION ACQUIRING APPARATUS AND CONTROL METHOD FOR THE OBJECT INFORMATION ACQUIRING APPARATUS

BACKGROUND OF THE INVENTION

Field of the Invention

The present invention relates to an object information acquiring apparatus that acquires internal information of an object and a method for controlling the same.

Description of the Related Art

As one of apparatuses that acquire internal information of an object using an acoustic wave, there is an ultrasonic image sensing apparatus. When a living body is irradiated with an ultrasonic wave, the ultrasonic wave propagates in the object to be reflected by tissue interfaces between living body tissues which have different acoustic properties (acoustic impedances). The ultrasonic image sensing apparatus receives an acoustic wave resulting from the reflection using a probe and reconstructs image data on the basis of the intensity of the acoustic wave, thereby allowing the internal information (shape information) of the object related to the acoustic properties to be visualized.

On the other hand, as a radiation-free/non-invasive image sensing apparatus similar to the ultrasonic image sensing apparatus, there is a photoacoustic image sensing apparatus. When an object is irradiated with measurement light such as pulse laser light, upon absorption of the measurement light in living body tissues in the object, an acoustic wave is generated. By receiving the generated acoustic wave with a probe and analyzing the acoustic wave, the photoacoustic image sensing apparatus can visualize the internal information (functional information) of the object related to an optical property.

Each of these apparatuses receives the acoustic wave coming from inside the object using the probe. However, when there is a region having a different acoustic impedance between the object and the probe, the acoustic wave is reflected by the region and an image cannot normally be reconstructed. Accordingly, in the apparatus which acquires internal information of the object using the acoustic wave, it is necessary to achieve an acoustic impedance match on a propagation path for the acoustic wave.

For example, in a living body information acquiring apparatus described in Japanese Patent Application Laid-open No. 2011-156208, an object is press-held using a holding plate and the gap between the object and the holding plate is filled with an acoustic matching material to achieve an acoustic impedance match between the object and a probe.

SUMMARY OF THE INVENTION

In the case of press-holding an object using a holding member as in the apparatus disclosed in Japanese Patent Application Laid-open No. 2011-156208, an air bubble (bubble of air) may be entrapped between the holding member and an object or between an acoustic matching member and the object. Since the acoustic impedance of air is significantly different from that of another substance, if an air bubble is present in a propagation path for an acoustic wave, the air bubble may cause incorrect measurement.

For example, when the entrapment of an air bubble occurs in a photoacoustic image sensing apparatus, an acoustic wave generated in a living body is interrupted by the air bubble and cannot reach a probe. When the entrapment of an air bubble occurs in an ultrasonic image sensing apparatus, a more pronounced situation is encountered in which an ultrasonic wave transmitted from a probe is not incident on an object but is directly reflected thereby, thus causing multiple reflection between the probe and the air bubble. In either case, the air bubble causes the generation of an image lacking information which should have inherently been obtained.

Thus, in an apparatus that acquires information on an object using an acoustic wave, measurement should be performed with attention to the entrapment of an air bubble. However, when the presence of an air bubble is noticed after measurement is performed, the measurement involving the pressing of an object needs to be performed again, which places a considerable burden on a subject under test.

The present invention has been achieved in view of such related-art problems and an object of the present invention is to provide an object information acquiring apparatus capable of detecting an entrapped air bubble.

The present invention in its one aspect provides an object information acquiring apparatus that transmits an acoustic wave to an object, and receives and analyzes the reflected acoustic wave to acquire internal information of the object, comprises a probe that transmits and receives the acoustic wave; a holding member disposed between the object and the probe to hold the object; and an air bubble detection unit that detects an air bubble present between the object and the holding member on the basis of an intensity of the acoustic wave received after a first time from the transmission by the probe, the first time being calculated on the basis of a time when the acoustic wave reaches a predetermined distance.

The present invention in its another aspect provides an object information acquiring apparatus that irradiates an object with light, and receives and analyzes a photoacoustic wave generated in the object to acquire internal information of the object, comprises a light irradiation unit that irradiates the object with the light; a probe that transmits an acoustic wave to the object and receives the acoustic wave reflected in the object and the photoacoustic wave generated in the object due to the light; a holding member disposed between the object and the probe to hold the object; and an air bubble detection unit that detects an air bubble present between the object and the holding member on the basis of an intensity of the acoustic wave received after a first time from the transmission by the probe, the first time being calculated on the basis of a time when the acoustic wave reaches a predetermined distance.

The present invention in its another aspect provides a method for controlling an object information acquiring apparatus including a probe that transmits an acoustic wave to an object and receives an acoustic wave from an object, and a holding member disposed between the object and the probe to hold the object, the object information acquiring apparatus receiving and analyzing the acoustic wave reflected in the object to acquire internal information of the object, the method comprises a transmission step of transmitting the acoustic wave from the probe to the object; a reception step of acquiring an intensity of the acoustic wave received after a first time from the transmission by the probe, the first time being calculated on the basis of a time when the acoustic wave reaches a predetermined distance; and an air bubble detection step of detecting an air bubble present between the object and the holding member on the basis of the acquired intensity of the acoustic wave.

The present invention can provide an object information acquiring apparatus capable of detecting an entrapped air bubble.

Further features of the present invention will become apparent from the following description of exemplary embodiments with reference to the attached drawings.

DESCRIPTION OF THE EMBODIMENTS

Figure 1:
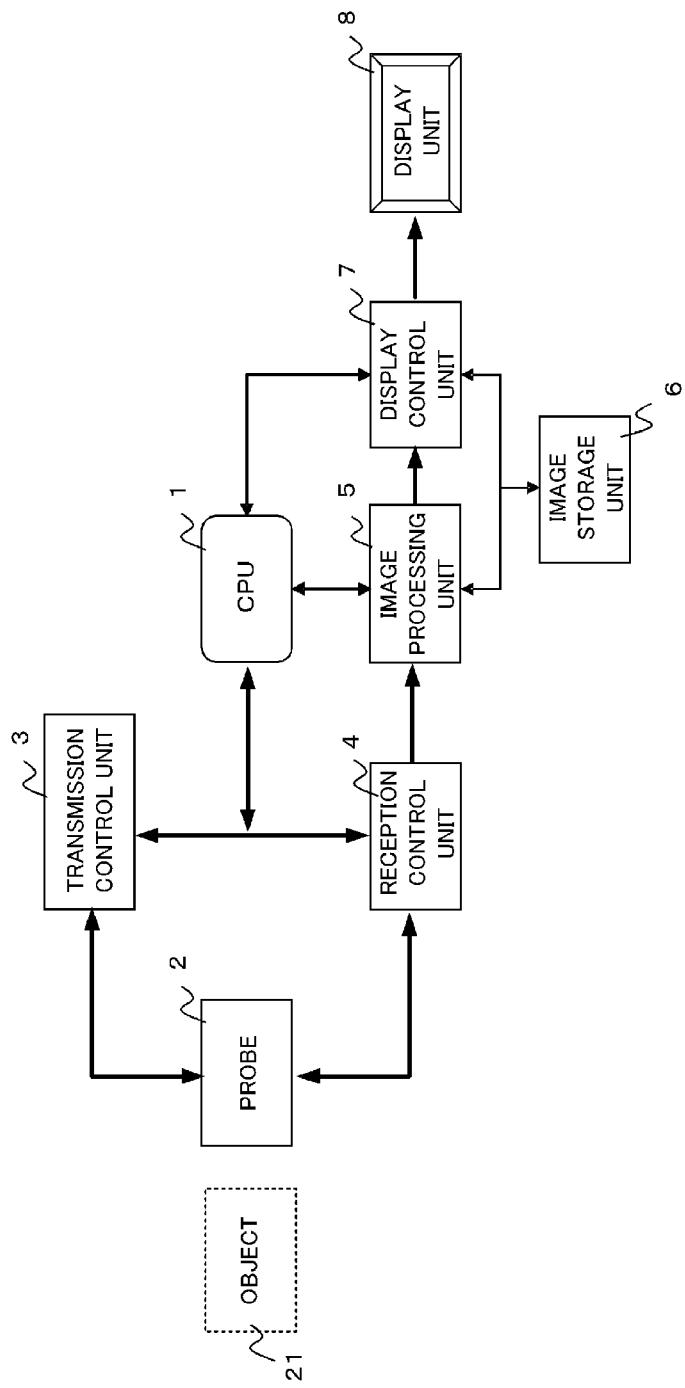
FIG. 1 is a view showing a configuration of an ultrasonic diagnostic apparatus in a first embodiment.

Referring now to the drawings, embodiments of the present invention will be described below in detail. Note that like components are denoted by like reference numerals in principle and a description thereof is omitted.

First Embodiment

An ultrasonic diagnostic apparatus according to the first embodiment of the present invention is an apparatus that transmits an ultrasonic wave to an object, receives the ultrasonic wave reflected in the object using a probe, and analyzes the received ultrasonic wave to image the internal shape information of the object related to an acoustic property.

<System Configuration>

Figure 2:
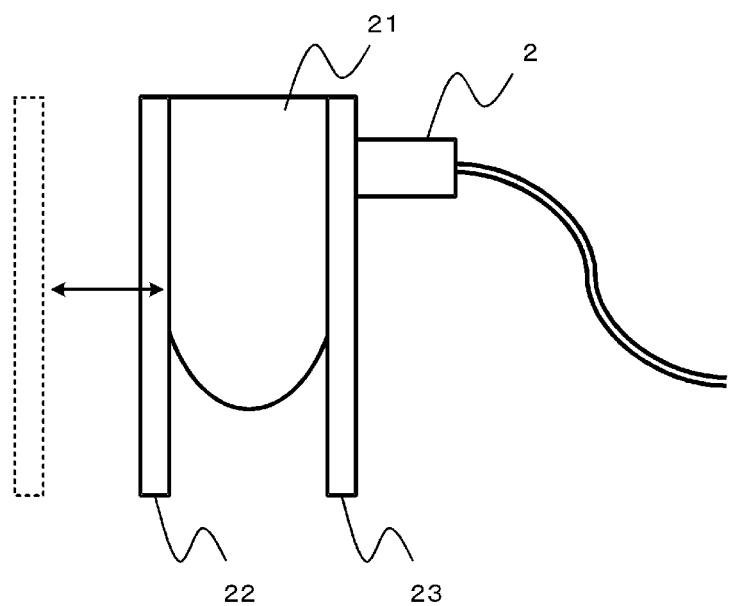
FIG. 2 is a schematic diagram of an object and the periphery thereof in the first embodiment.

Referring to FIGS. 1 and 2, a configuration of the ultrasonic diagnostic apparatus according to the first embodiment will be described. The ultrasonic diagnostic apparatus according to the first embodiment has a CPU 1, a probe 2, a transmission control unit 3, a reception control unit 4, an image processing unit 5, an image storage unit 6, a display control unit 7, and a display unit 8.

The CPU 1 is an arithmetic processing device that controls the apparatus. By executing a program stored in a nonvolatile memory not shown in the CPU1, control over each of means described later is performed.

The probe 2 is a probe having an embedded acoustic element, which is means for performing transmission/reception of an ultrasonic beam to/from an object. As a typical ultrasonic probe, a conversion element using a piezoelectric ceramic (PZT), a conversion element of a capacitive microphone type, or the like is used. Note that the probe 2 may also be a plurality of acoustic elements arranged in one dimension or two dimensions.

Alternatively, a capacitive micromachined ultrasonic transducer (CMUT), a magnetic MUT (MMUT) using a magnetic film, or the like can also be used. Any type of probe, such as a piezoelectric MUT (PMUT) having a piezoelectric thin film, may be used.

The transmission control unit 3 is means for generating a signal to be applied to the acoustic element embedded in the probe 2 to control the frequency and acoustic pressure of an ultrasonic wave to be transmitted.

The reception control unit 4 is means for converting an ultrasonic wave detected by the acoustic element embedded in the probe 2 to an analog electric signal. Specifically, the reception control unit 4 includes an amplifier, an analog-digital converter (ADC), and the like each formed of an electric circuit. To efficiently acquire data, it is desirable to provide the same number of amplifiers and ADCs as that of the elements provided in the probe 2. However, it may also be possible to prepare one amplifier and one ADC and alternately and repeatedly use the amplifier and the ADC in succession.

The image processing unit 5 is means for subjecting the signal obtained in the reception control unit 4 to A/D conversion to reconstruct the signal and generate an image. The image storage unit 6 is means for temporarily storing the generated image. The display control unit 7 is means for scan-converting an image to convert the image to a video signal. The display unit 8 is a monitor that displays an image.

When the probe 2 is brought into contact with an object 21 (which is a living body in the present embodiment) and an ultrasonic wave is transmitted thereto, the ultrasonic wave travels in the object in an extremely short time to be reflected by a boundary between different media in contact (i.e., having different acoustic impedances) and returned as a reflected wave (hereinafter referred to as a reflected echo). Accordingly, by receiving the reflected echo with the probe 2 and calculating a distance from the time from the transmission of the ultrasonic wave to the reception of the reflected echo, the distributions of substances in the living body can be imaged.

Note that the ultrasonic diagnostic apparatus according to the present embodiment has a holding member that holds the object, though not shown in FIG. 1.

FIG. 2 is a schematic diagram of the object and the periphery thereof. When measurement is performed, a subject under test is placed in a prone position and a breast mass 21 as the object is held by the holding member (between a pressing plate 22 and a holding plate 23). The distance between the pressing plate 22 and the holding plate 23 is adjustable to be able to press-hold the object into a proper shape for measurement. Each of the plates is fixed in a state where the object is held thereby, and the probe 2 receives the reflected echo resulting from reflection in the object via the holding plate 23.

Note that the probe 2 is configured to be able to perform two-dimensional scanning in an in-plane direction of the holding plate 23 using a scanning mechanism not shown.

To perform precise measurement using the ultrasonic diagnostic apparatus, the holding plate 23 located on the side of the object closer to the probe needs to be in close contact with the object 21. If there is an air bubble entrapped between the holding plate 23 and the object 21, acoustic impedances on both sides of the air bubble are different and therefore precise measurement cannot be performed. Accordingly, the ultrasonic diagnostic apparatus according to the present embodiment detects the air bubble entrapped between the holding plate 23 and the object 21 in accordance with a method described later.

<Outline of Measurement>

Next, a method of detecting an air bubble will be described in detail in conjunction with the description of a method of performing measurement on an object.

Figure 3:
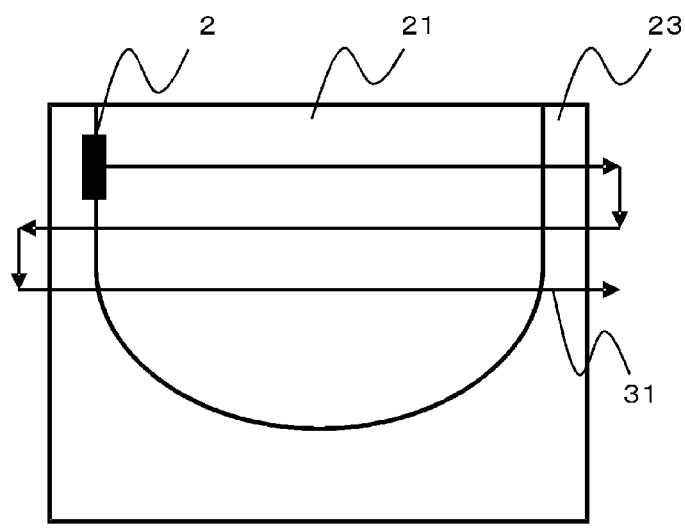
FIG. 3 is a view showing the scanning path of a probe in the first embodiment.

FIG. 3 is a view in which the object 21 is viewed from the front side of the holding plate 23. The reference numeral 31 shown in FIG. 3 shows a movement path when the probe 2 is caused to perform scanning. When measurement is initiated, the CPU 1 repeats the operation of rightwardly moving the probe 2 along an in-plane direction of the holding plate 23 till the right end portion thereof is reached, downwardly moving the probe 2 upon reaching of the right end portion, and then leftwardly moving the probe 2. Thus, the probe is caused to mechanically scan the entire measurement region.

The scanning method may also be a method which intermittently moves the probe or a method which continuously moves the probe. By acquiring an image while performing scanning, at any point on the movement path 31, a two-dimensional ultrasonic image can be acquired.

Figure 4:
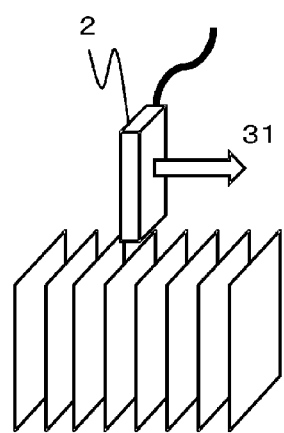
FIG. 4 is a view illustrating acquisition of images in the first embodiment.

FIG. 4 is a view showing ultrasonic images that can be acquired by scanning. The laterally arranged planes represent a plurality of ultrasonic images (B-mode images) acquired. When the probe is intermittently moved, each of the ultrasonic images is acquired at the time when the probe stops. When the probe is continuously moved, the ultrasonic images are acquired at given periods.

By arranging the plurality of two-dimensional ultrasonic images acquired, a three-dimensional ultrasonic image of the entire measurement region can be generated.

Figure 5:
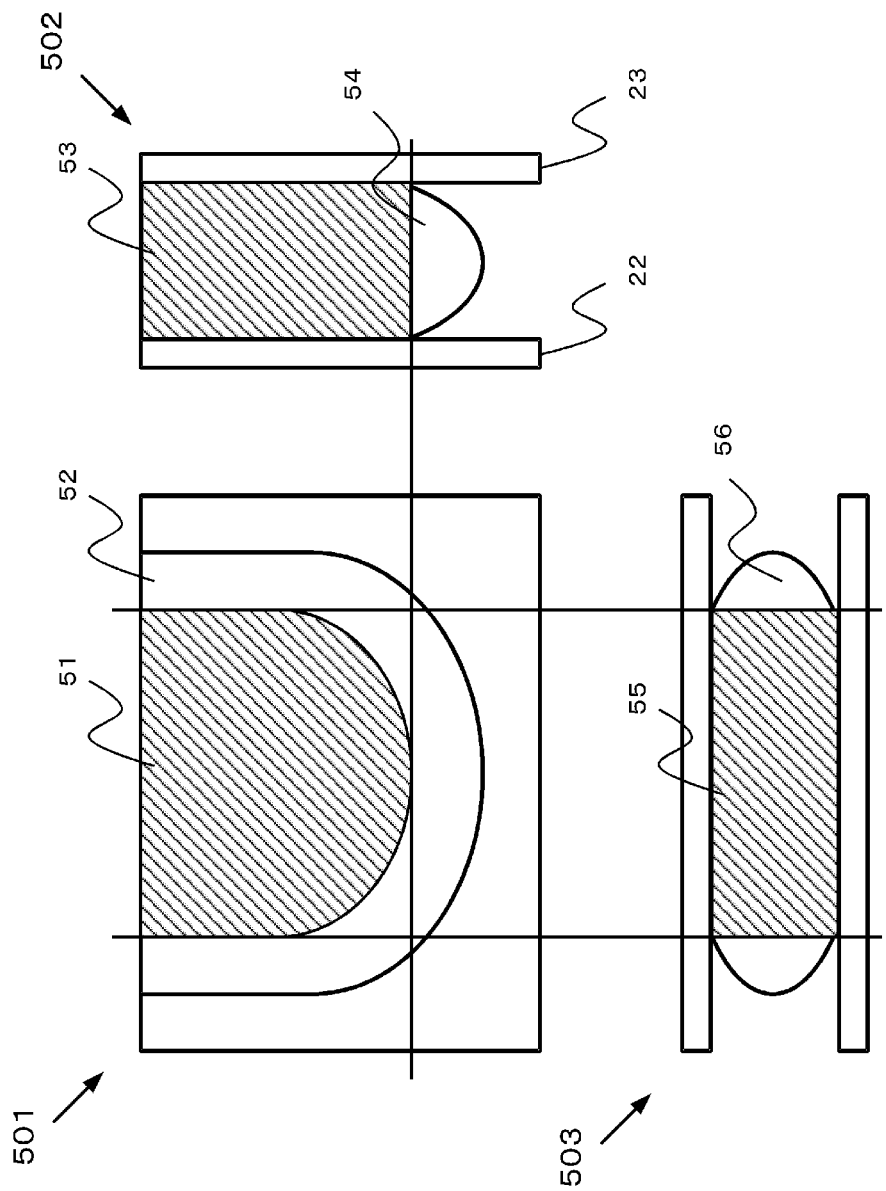
FIG. 5 is a 3-plane view each showing a state in which the object is held in the first embodiment.

Specific examples are shown below. FIG. 5 is a 3-plane view representing the actual shapes of the object when the object 21 is held between the holding plate 23 and the pressing plate 22. The B-mode image that can be obtained by scanning the object with the probe is the image in the plane shown by a symbol 502. By arranging the images, the three-dimensional ultrasonic image can be constructed and, by slicing the three-dimensional ultrasonic image along an arbitrary plane, two-dimensional ultrasonic images corresponding to various planes can be generated.

For example, when slicing is performed along a plane parallel with a surface of the holding plate, the image in the plane shown by a symbol 501 can be generated. The image thus obtained by slicing the three-dimensional ultrasonic image along a plane perpendicular to the direction of transmission of the ultrasonic wave is referred to as a C-mode image.

On the other hand, when slicing is performed along a plane parallel with a chest wall, the image in the plane shown by a symbol 503 can be generated. While the image obtained by slicing the three-dimensional ultrasonic image along the plane perpendicular to the direction of transmission of the ultrasonic wave is referred to as the C-mode image, an image generated by slicing the three-dimensional ultrasonic image along an arbitrary plane is called a slice image in the present embodiment.

If the function of generating 3-plane slice images using a volume rendering function is used, it is also possible to generate the 3-plane slice images by specifying an arbitrary position (X-, Y-, and Z coordinates) in the object and display the 3-plane slice images as the image data.

When measurement is performed using the ultrasonic diagnostic apparatus, it is important whether or not the object is in close contact with the holding plate. When there is a region where the object is not in close contact with the holding plate, information on the region and the periphery thereof is absent. This is because, since the acoustic impedance of air is several hundred times larger than that of the living body, the ultrasonic wave is reflected without being incident thereon. As a result, ultrasonic images can be generated for regions (regions 51, 53, and 55) where the object is in sufficiently close contact with the holding plate, but no ultrasonic image can be generated for regions (regions 52, 54, and 56) where the object is not in close contact with the holding plate. Even though the object seems to be in close contact with the holding plate, when an air bubble is entrapped therebetween, the ultrasonic wave is reflected by the air bubble portion, and therefore a normal image cannot be obtained.

<Outline of Air Bubble Detecting Process>

Figure 6:
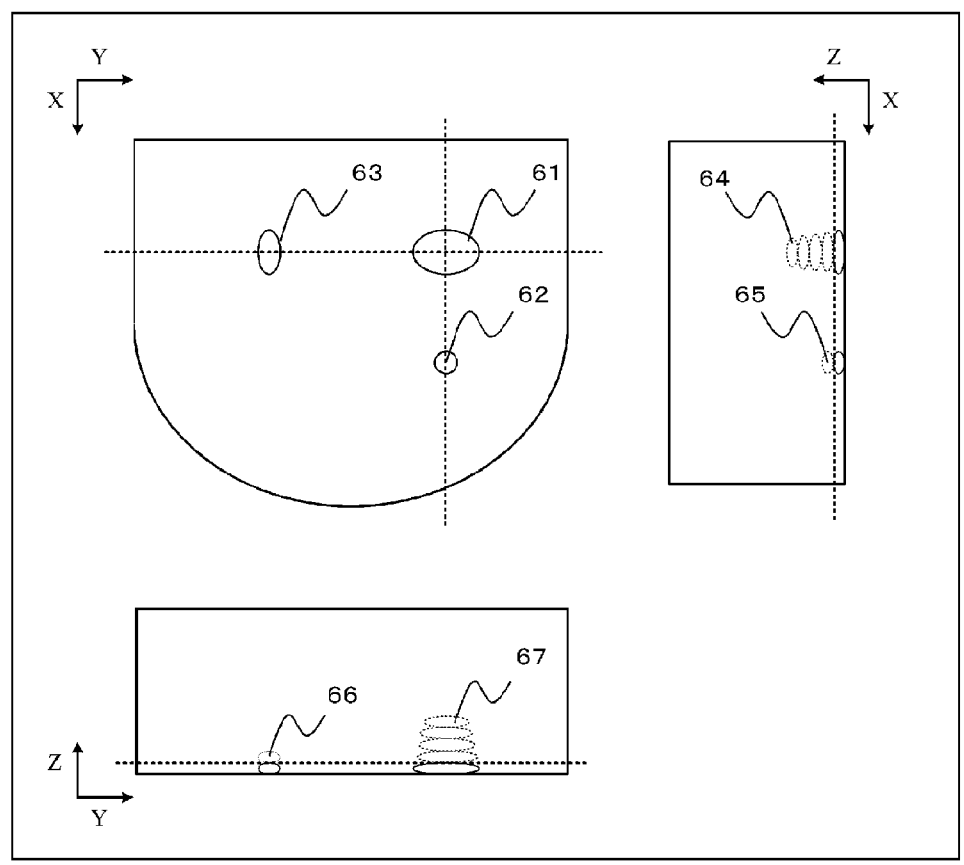
FIG. 6 is a view showing 3-plane slice images when an air bubble is entrapped in the first embodiment.

FIG. 6 is a view showing respective slice images corresponding to the regions 51, 53, and 55 when an air bubble is entrapped between the contacting portions of the object 21 and the holding plate 23. The dotted lines in the drawings correspond to the respective slice cross sections of the images.

Here, it is assumed that there are three entrapped air bubbles 61, 62, and 63. When the air bubbles are entrapped, the acoustic wave transmitted from the probe is returned by full reflection toward the probe without entering the air bubbles. The reflected acoustic wave incurs some reflection even on the probe side and decays, while being repeatedly reflected between the probe and the air bubbles. That is, the ultrasonic wave is repeatedly incident on the probe to result in false images (denoted by reference numerals 64, 65, 66, and 67) appearing in the direction of transmission of the ultrasonic wave over the slice images. That is, since the information on the regions is missing, the internal information of the object cannot normally be acquired. Regions where the false images appear are hereinafter referred to as multiple reflection regions.

Next, a method for detecting an air bubble will be described. Since an air bubble is entrapped between the object 21 and the holding plate 23, by acquiring the C-mode image of a predetermined depth in a plane parallel with the holding plate 23, the air bubble can be detected. The predetermined depth may be set appropriately on the basis of the size of the air bubble desired to be detected.

The C-mode image is the image generated on the basis of the intensity of the received ultrasonic wave. On the other hand, when multiple reflection occurs due to an air bubble, the reflected ultrasonic wave is repeatedly incident on the probe so that an ultrasonic wave having an intensity over the upper limit of the input range of the probe is received from a region where the multiple reflection has occurred. Accordingly, if the process of digitizing the acquired C-mode image is performed using a value close to the upper limit of the input range as a threshold value, an image representing the shape of the air bubble can be acquired.

Figure 7:
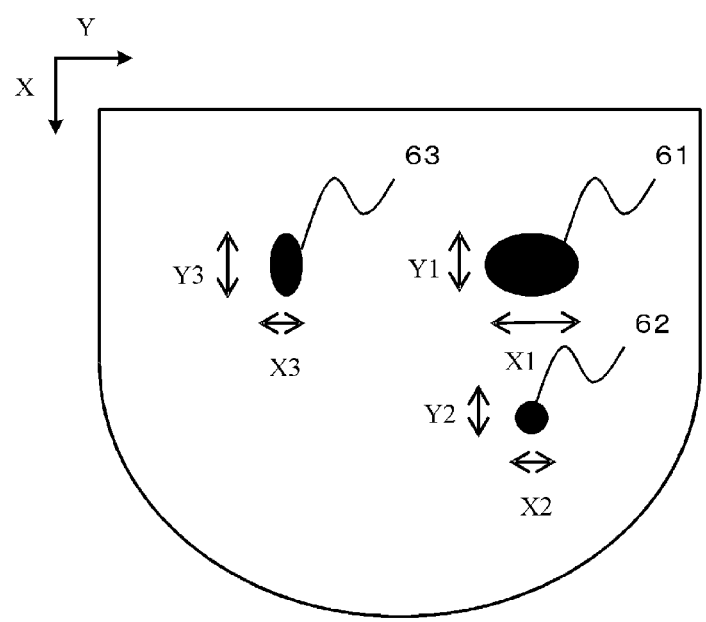
FIG. 7 is a view showing a digitized image in the first embodiment.

FIG. 7 shows an image obtained by digitizing the image corresponding to the X-Y plane of the slice image shown in FIG. 6. The image is obtained by slicing the three-dimensional ultrasonic image at the Z-coordinate close to a plane in which the object 21 is in contact with the holding plate 23. From the image, it can be seen that the air bubbles are present at the positions denoted by the reference numerals 61, 62, and 63.

Depending on the sizes and shapes thereof, air bubbles are divided into those of a type that affects measurement and those of a type that does not affect measurement. When the detected air bubble is of the type that affects measurement, it is preferable to halt the measurement and press-hold the object again. When the air bubble is of the type that does not affect the measurement, the measurement can be continued. Here, a description will be given of a method of determining whether or not the detected air bubble is of the type that affects the measurement.

An air bubble does not necessarily have an exactly circular shape. Depending on how air is entrapped when the object and the holding plate are brought into close contact, the shape thereof varies. For example, the air bubble may have a truly circular shape, an ellipsoidal shape, or another deformed shape.

Accordingly, the lengths of the detected air bubble in a direction along an X-axis (first direction in the present invention, which is hereinafter referred to as the X-direction) and in a direction along a Y-axis (second direction orthogonal to the first direction, which is hereinafter referred to as the Y-direction) are measured. Here, it is assumed that the length of the air bubble 61 in the X-direction is X1 and the length thereof in the Y-direction is Y1. Likewise, it is also assumed that the lengths of the air bubble 62 in the X-direction and the Y-direction are X2 and Y2 and the lengths of the air bubble 63 in the X-direction and the Y-direction are X3 and Y3. The air bubble 61 has a laterally elongated ellipsoidal shape. The air bubble 62 has a truly circular shape. The air bubble 63 has a vertically elongated ellipsoidal shape. That is, the relationships between the lengths are given by X1>Y1, X2=Y2, and X3<Y3. Note that, when the shapes of the air bubbles are other than circles, the maximum widths (maximum diameters) in the X-direction and the Y-direction may also be measured.

Examples of the method of determining whether or not the detected air bubble is of the type that affects the measurement include the following methods.

(1) Method which Estimates Area of Air Bubble and Makes Determination Using Estimated Area As the area of an air bubble is larger, the intensity of the repeatedly reflected acoustic wave is higher. For example, in the example of FIG. 6, multiple reflection (denoted by the reference numeral 64) resulting from the air bubble 61 reaches the portion deeper than the portion reached by multiple reflection (denoted by the reference numeral 65) resulting from the air bubble 62. Therefore, when the area of the air bubble is estimated and the estimated area is larger than a predetermined threshold value, the air bubble can be determined to be of the type that affects the measurement. If the lengths of the air bubble in the X-direction and the Y-direction are $X_e$ and $Y_e$, the area of the air bubble can be approximated to $\pi X_e Y_e/4$.

(2) Method which Makes Determination Using Shorter One of Lengths of Air Bubble in X-Direction and Y-Direction On the other hand, since an acoustic wave has the property of reaching the air bubble from around the outer peripheral portion thereof, when the area of the air bubble is large but the width thereof is sufficiently small, the multiple reflection region does not reach a deep portion. Accordingly, if the lengths of the air bubble in the X-direction and the Y-direction are $X_e$ and $Y_e$ and the shorter one of the lengths $X_e$ and $Y_e$ is longer than a predetermined threshold value, it can be determined that the air bubble affects the measurement. In the present embodiment, the presence or absence of the air bubble that affects the measurement, i.e., the air bubble that needs to be removed is determined in accordance with the method (2).

Of the lengths of the air bubbles 61, 62, and 63 in the X-direction and the Y-direction, the shorter lengths are Y1, X2 (=Y2), and X3. Among them, X2 and X3 are assumed to be shorter than the threshold value and only Y1 is assumed to be longer than the threshold value. In this case, only the air bubble 61 is determined to be of the type that affects the measurement.

<Flow Chart of Air Bubble Detection Process>

Figure 8:
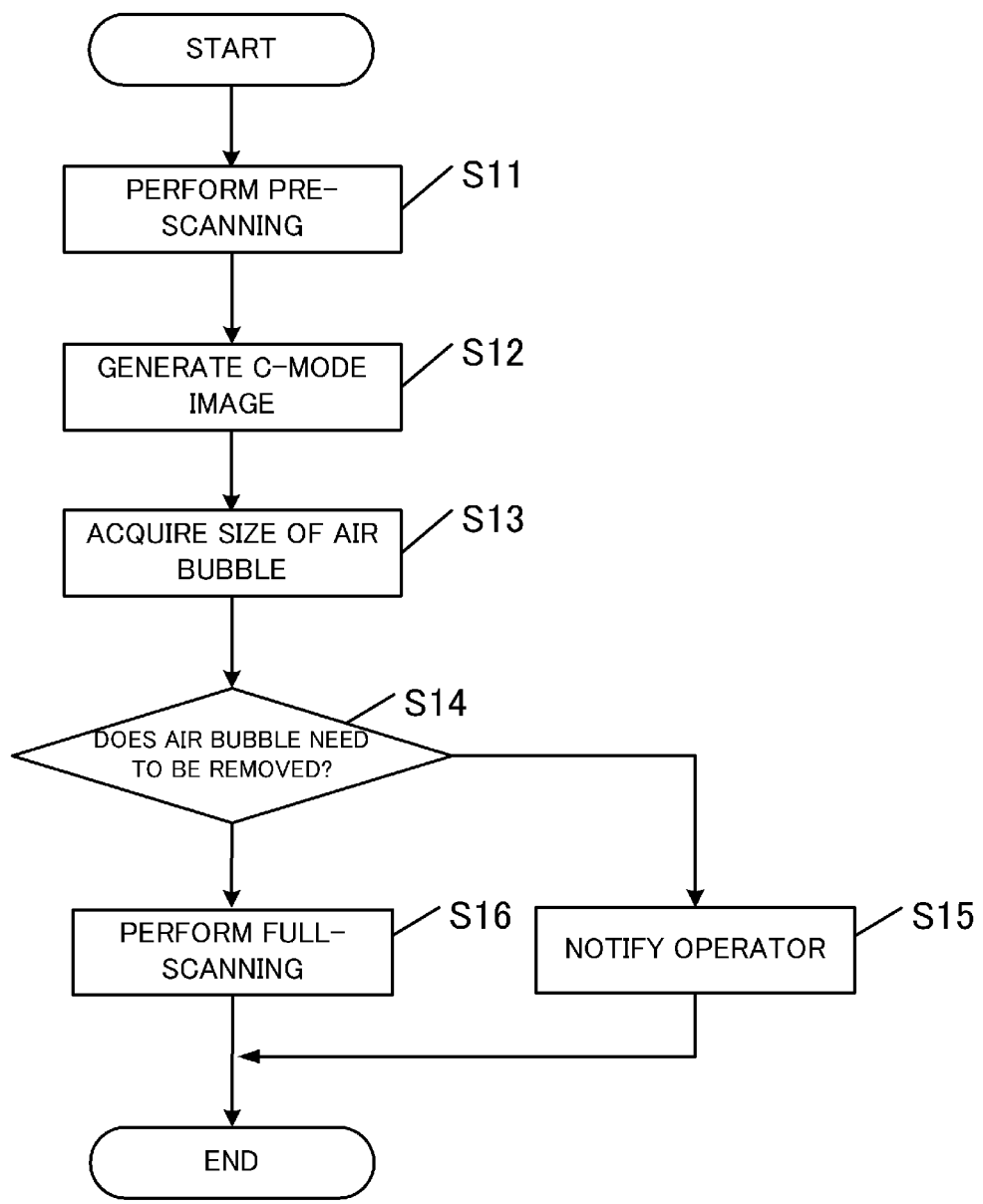
FIG. 8 is a view showing the flow of air bubble determination in the first embodiment.

FIG. 8 is a view showing the flow of air bubble determination performed by the ultrasonic diagnostic apparatus (CPU 1) in the first embodiment.

When the process is started, in Step S11, pre-scanning is performed using the probe 2, the transmission control unit 3, and the reception control unit 4. Hereinafter, scanning performed in advance to detect an air bubble is referred to as pre-scanning and scanning in normal measurement is referred to as full scanning.

Then, an ultrasonic wave acquired in the pre-scanning is reconstructed using the image processing unit 5 to generate a C-mode image resulting from slicing along a plane parallel with the holding plate 23 (Step S12). The depth at which the slicing is performed is sufficient as long as the depth allows the entrapment of an air bubble to be assumed. For example, a depth obtained by adding an extra to the thickness of the holding plate 23 can be used. The generated C-mode image is digitized and temporarily stored in the image storage unit 6. Here, an image resulting from the digitization is referred to as a digitized image.

Next, in Step S13, the size of the air bubble is acquired from the stored digitized image. In the present embodiment, the shorter one of the lengths of the detected air bubble in the X-direction and the Y-direction is acquired. Then, the acquired value is compared to the threshold value (Step S14) and it is determined whether or not the air bubble needs to be removed.

Here, when the air bubble needs to be removed, a notification is given to an operator (Step S15). Upon receipt of the notification, the operator performs the operation of holding the object again. After the operation, the process is resumed in Step S11.

When no air bubble is detected or when there is an air bubble but it is determined in Step S14 that the air bubble need not be removed, the pre-scanning shifts to the full-scanning without giving a notification (Step S16).

By thus performing the pre-scanning before performing measurement, the ultrasonic diagnostic apparatus according to the first embodiment can determine the presence or absence of an air bubble that needs to be removed.

In addition, since the pre-scanning can be completed in a shorter time than the full scanning, a total physical burden on a subject under test can be reduced.

A description will be given of the reason for that.

In normal ultrasonic measurement, a probe needs to move, while receiving an ultrasonic echo reflected at a desired depth in an object. That is, as the desired depth is deeper, the reach of the ultrasonic wave and the reach of the reflected echo is later so that the speed of movement of the probe is lower.

On the other hand, a plane along which slicing is performed in Step S12 is located in the vicinity of the plane in which the object 21 is in contact with the holding plate 23. That is, as long as the ultrasonic wave can be acquired from the depth at which the plane is located, an image for performing air bubble determination can be generated. Here, the depth is referred to as a reaching depth D. The reaching depth D is a sum of the thickness of the holding plate and an extra and is therefore far shorter than a reaching depth in the normal measurement.

In the pre-scanning in the first embodiment, the round-trip time (a first time in the present invention) of the ultrasonic wave is calculated on the basis of the reaching depth D and, after the lapse of the time (after the first time), the probe can be moved. That is, since the time required for retrieving the reflected echo corresponding to one slice is shorter than during the full scanning, the probe can be moved at a speed higher than during the full scanning and the detection of the air bubble can be completed in a shorter time.

Modification of First Embodiment

The first embodiment is the ultrasonic diagnostic apparatus, but the present invention is also applicable to a photoacoustic measurement apparatus.

The photoacoustic measurement apparatus is an apparatus which irradiates an object with pulse light generated from a light source and emitted from the light irradiation unit, receives a photoacoustic wave (which is typically an ultrasonic wave) generated through the absorption of the light in the object with a probe, and analyzes the received acoustic wave to visualize the internal tissue of the object. In the photoacoustic measurement apparatus also, if an air bubble is entrapped between the probe and the object, information cannot normally be acquired.

Accordingly, it may also be possible to add means for transmitting an ultrasonic wave from the probe to the object and detect an air bubble present between the probe and the object by the same method as in the first embodiment. As the ultrasonic wave to be transmitted to the object, an ultrasonic wave in the same frequency band as that of the acoustic wave generated in the object can be used.

Thus, the present invention is applicable to any apparatus that acquires information on the object using an ultrasonic wave.

Second Embodiment

The ultrasonic diagnostic apparatus according to the first embodiment can detect the air bubble entrapped between the object 21 and the holding plate 23. However, there is a case where measurement is performed by interposing an acoustic matching material for achieving an acoustic impedance match between the object and the holding plate. In such a case, air bubbles may possibly be entrapped between the object and the acoustic matching material and between the acoustic matching material and the holding plate. To respond to such a case, the second embodiment acquires slice images corresponding to a plurality of different planes and performs the detection of an air bubble.

A configuration of an ultrasonic diagnostic apparatus according to the second embodiment is the same as in the first embodiment.

Figure 9:
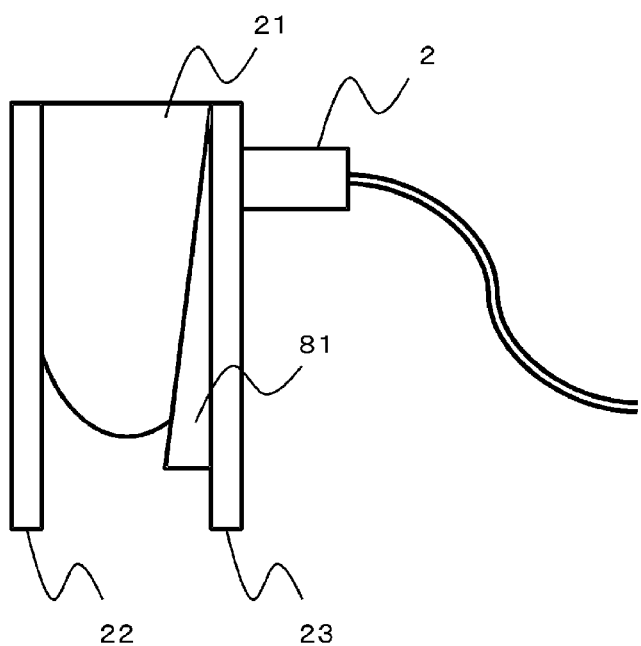
FIG. 9 is a schematic diagram of an object and the periphery thereof in a second embodiment.

FIG. 9 is a schematic diagram of an object and the periphery thereof in the second embodiment.

In the second embodiment, between the object 21 and the holding plate 23, an acoustic matching material 81 is additionally provided. The acoustic matching material is a material having an acoustic impedance equal to that of the object. By additionally providing the acoustic matching material 81, it is possible to perform ultrasonic measurement even on regions where the holding plate is not in close contact with the object, such as the regions 52, 54, and 56 in FIG. 5. The acoustic matching material 81 is a second holding member in the present invention.

As a typical material used as the acoustic matching material, there is a water bag. The water bag is obtained by forming a sheet-like elastomer having a thickness of about 30 micrometers into a bag and filling the hollow portion thereof with a material having an acoustic impedance similar to that of the object. Examples of the filling material include water, a sol, and a gel. However, the material of the water bag, the thickness thereof, and the material contained therein are not limited thereto.

Figure 10:
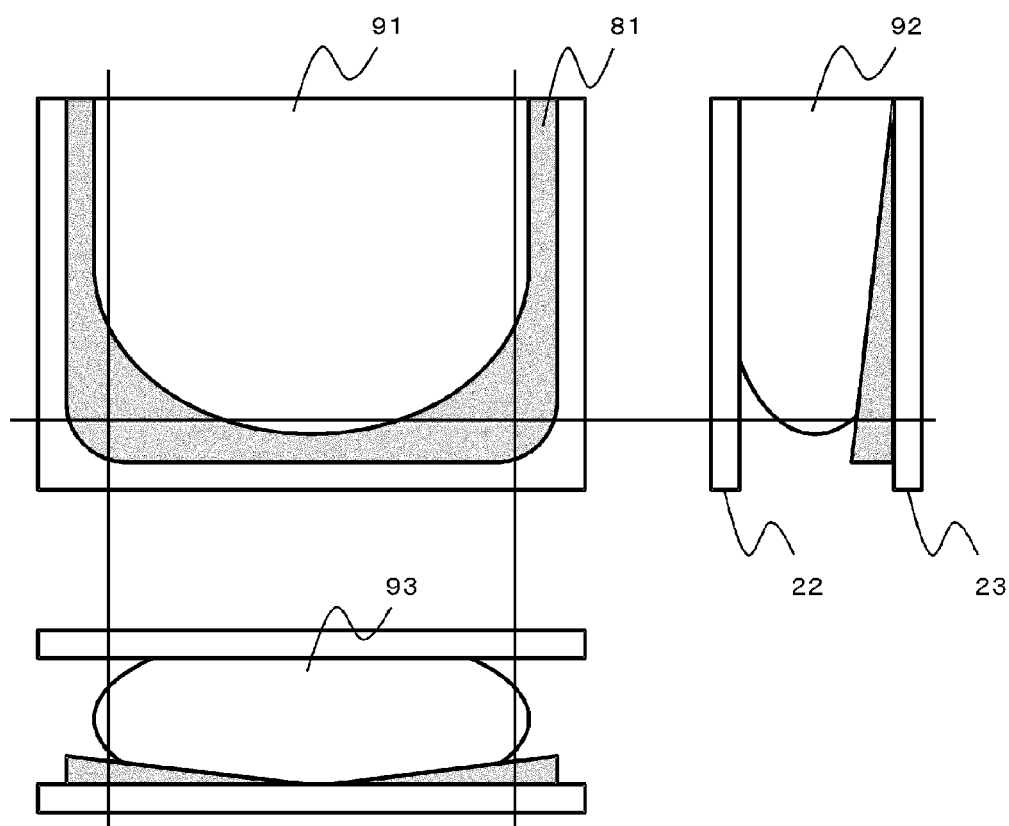
FIG. 10 is a 3-plane view each showing a state in which the object is held in the second embodiment.

FIG. 10 is a 3-plane view when the acoustic matching material 81 is inserted in the gap between the object 21 and the holding plate 23. The object of inserting the acoustic material is to bring the floating edge portion of the object into close contact with the holding plate 23 so that the acoustic matching material capable of holding the object in a U-shaped configuration is most preferred. However, if the acoustic matching material is formed in a U-shaped configuration, it becomes necessary to prepare several sizes in accordance with shapes. Accordingly, it is appropriate to form the acoustic matching material of a flexible member having a single-sheet configuration and bring the object into close contact with the holding plate using a pressing force generated when the object is held.

When measurement is performed with the acoustic matching material 81 being attached to the holding plate 23, an air bubble may be entrapped in a plane in which the acoustic matching material is in contact with the holding plate. In addition, when the object is held, an air bubble may be entrapped in a plane in which the object 21 is in contact with the acoustic matching material 81. Therefore, the entrapment of an air bubble should be checked for each of the planes.

Figure 11:
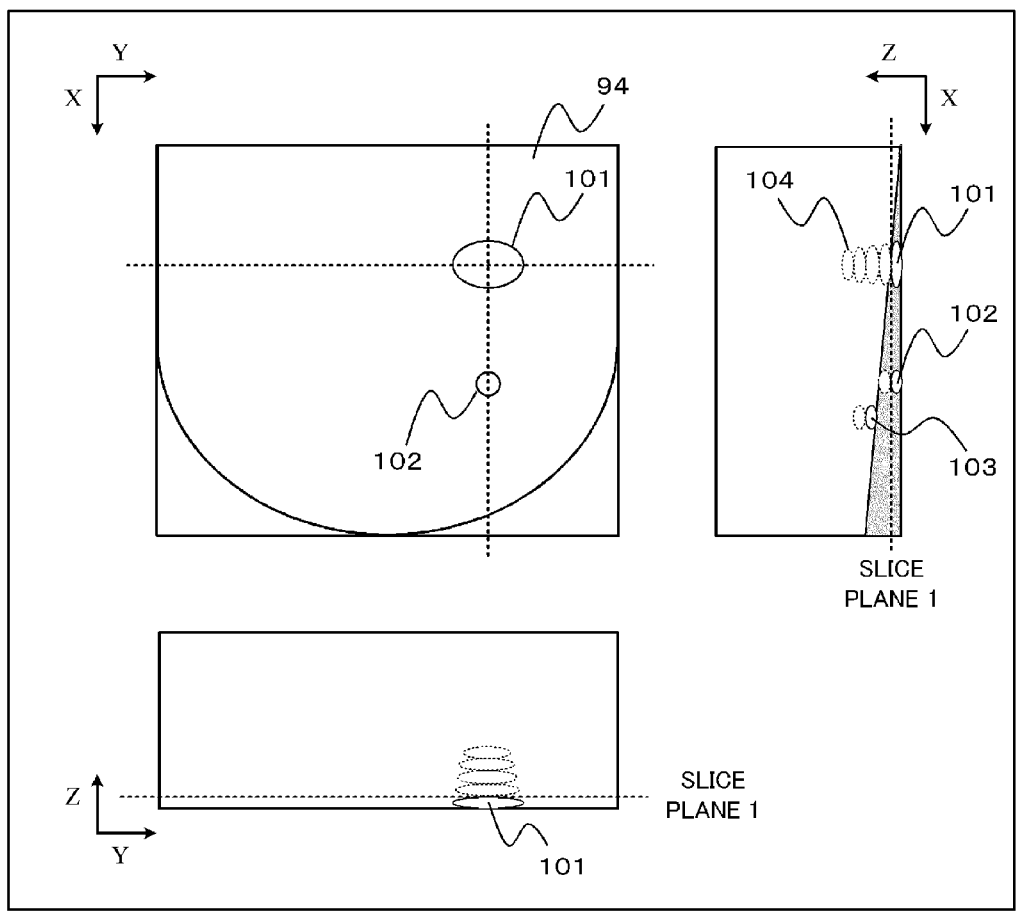
FIG. 11 is a view showing 3-plane slice images when an air bubble is entrapped in the second embodiment.

FIG. 11 is a view showing 3-plane slice images when air bubbles are entrapped between the contacting portions of the acoustic matching material 81 and the holding plate 23 and between the contacting portions of the holding plate 23 and the object 21. The dotted lines in the drawings correspond to the respective slice cross sections of the images. Here, it is assumed that the air bubbles are entrapped in the plane in which the acoustic matching material is in contact with the holding plate and in the plane in which the acoustic matching material is in contact with the object.

A C-mode image 94 shown in FIG. 11 is an image obtained by slicing a three-dimensional ultrasonic image along a plane parallel with the holding plate 23. In the present embodiment, the plane is referred to as a slice plane 1.

By using the image, it is possible to detect air bubbles 101 and 102 that are entrapped between the holding plate and the acoustic matching material.

However, in the C-mode image 94, the air bubbles 101 and 102 are observed, but an air bubble 103 entrapped between the acoustic matching material and the object is not observed. This is because the place in which the air bubble is entrapped is away from the slice plane 1 in the Z-axis direction.

The acoustic matching material 81 is obliquely in contact with the object. Therefore, to detect the air bubble which is entrapped between the object and the acoustic matching material, it is necessary to further acquire a slice image obtained by slicing the three-dimensional ultrasonic image along a plane parallel with the plane in which the acoustic matching material is in contact with the object. In the present embodiment, the plane is referred to as a slice plane 2.

Figure 12:
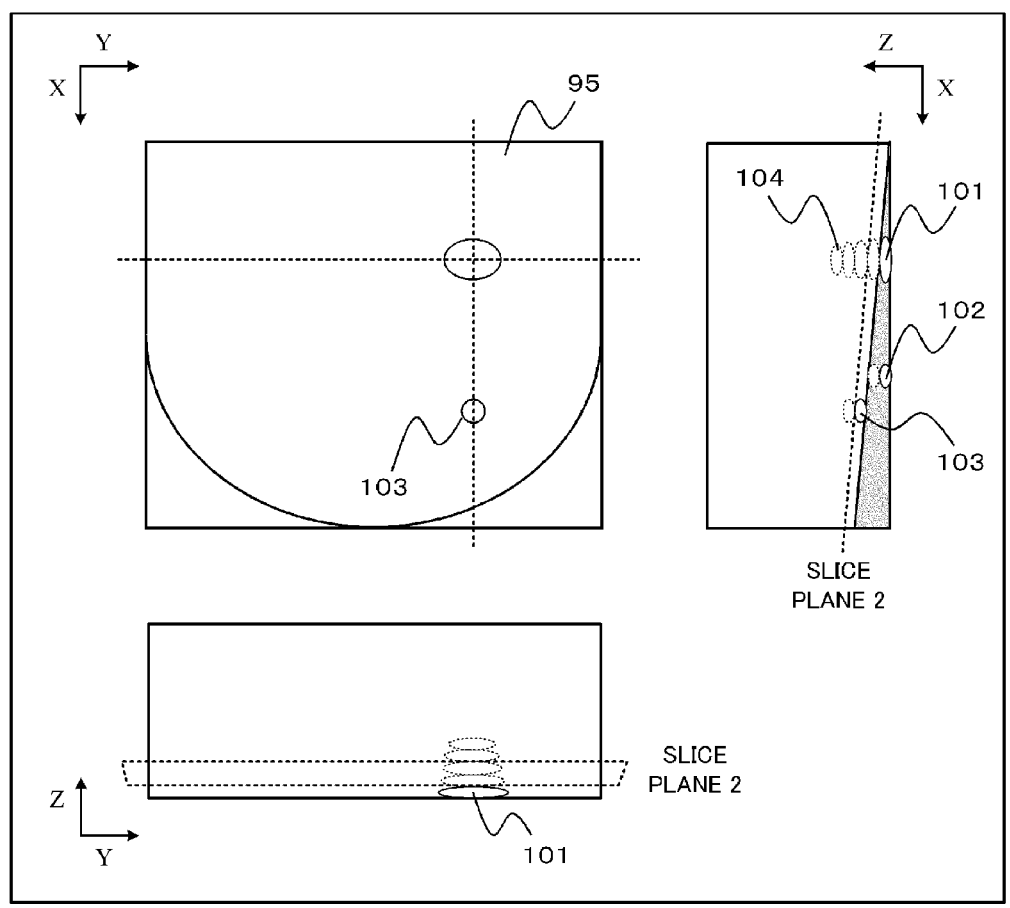
FIG. 12 is a view showing 3-plane slice images when an air bubble is entrapped in the second embodiment.

A slice image 95 shown in FIG. 12 is an image obtained by slicing the three-dimensional ultrasonic image along the slice plane 2 extending along the plane in which the acoustic matching material is in contact with the object. In this manner, the air bubble 103 entrapped between the object and the acoustic matching material can be detected.

Figure 13A:
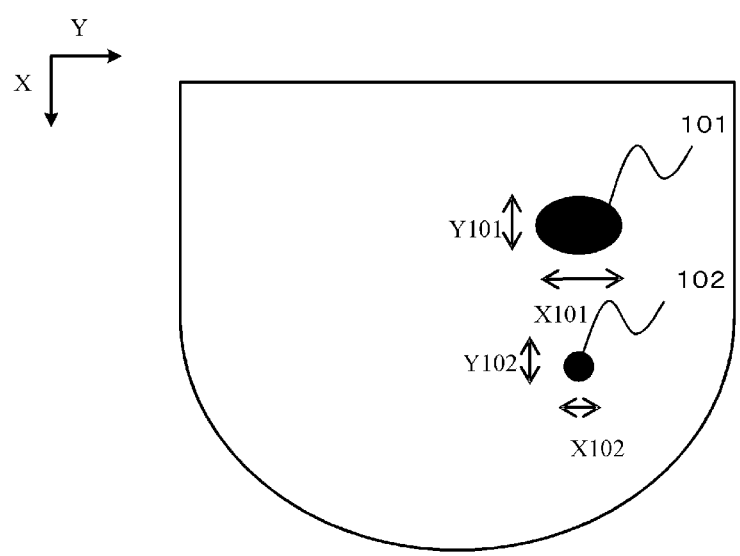
FIGS. 13A and 13B are views showing digitized images in the second embodiment.
Figure 13B:
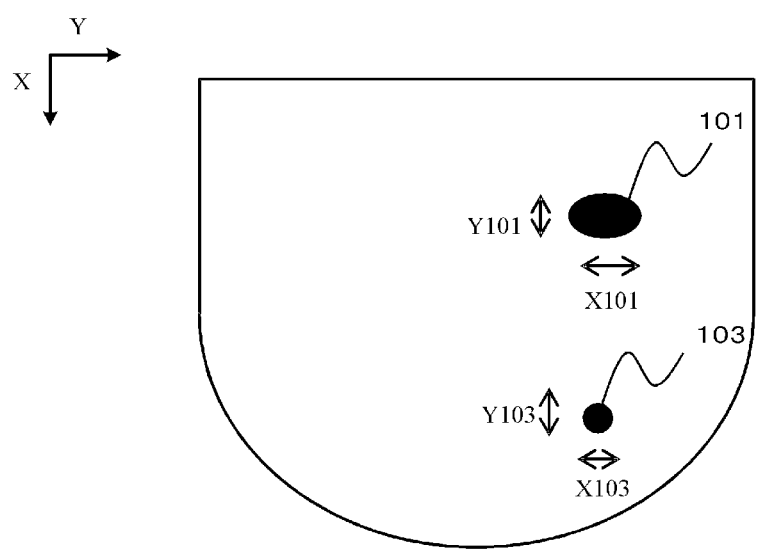

FIG. 13A shows a digitized image generated from the C-mode image resulting from slicing along the slice plane 1. FIG. 13B shows a digitized image generated from a slice image resulting from slicing along the slice plane 2. Thus, in the second embodiment, by generating the slice images resulting from slicing at a plurality of places in Step S12, it is possible to detect the air bubbles entrapped in a plurality of places such as between the object and the acoustic matching material and between the acoustic matching material and the holding plate. Note that the process subsequent to the generation of the digitized image (subsequent to Step S13) is the same as in the first embodiment except that the plurality of images are to be processed.

Note that, since multiple reflection 104 resulting from the air bubble 101 has reached a deep region, the image resulting from the air bubble 101 is observed in each of FIGS. 13A and 13B. In such a case, it is impossible to specify in which one of the contact planes the air bubble is entrapped.

Accordingly, in the present embodiment, when the images resulting from the air bubbles appear at the same positions in the both digitized images, the sizes thereof are compared to each other and it is determined that the air bubble is present in the plane with the larger image. In the present embodiment, the image appearing in FIG. 13A is larger, and therefore it is determined that the air bubble 101 is present between the acoustic matching material and the holding plate.

Thus, in the second embodiment, the detection of the air bubbles is performed using the plurality of slice images. As a result, even when there are two or more contact planes in which air bubbles may possibly be entrapped, the air bubbles can precisely be detected.

(Modification)

Note that the description of each of the embodiments is illustrative in describing the present invention and the present invention can be practiced by being modified or combined within the scope not departing from the gist of the invention. The present invention can also be practiced as a method for controlling an object information acquiring apparatus including at least a part of the foregoing process. The foregoing process and means can be implemented by being freely combined unless a technical contradiction is encountered.

Figure 14:
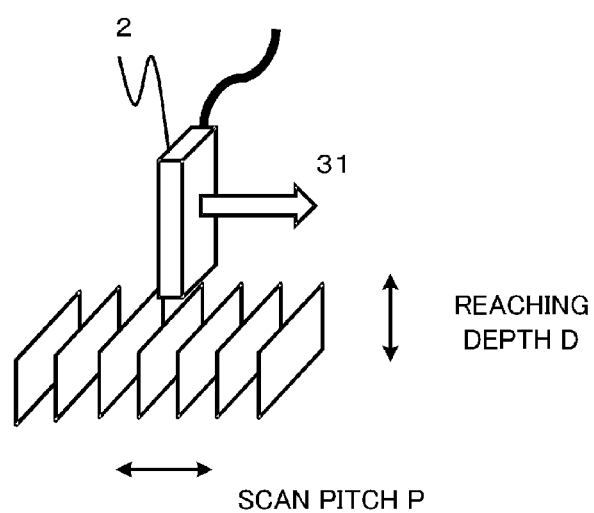
FIG. 14 is a view showing scanning with a probe in a third embodiment.

For example, in the pre-scanning, a resolution can be set lower than during the normal measurement. The set resolution is appropriate as long as the resolution is sufficient to allow an air bubble to be detected. That is, by increasing the interval of the scan pitch P shown in FIG. 14, the speed of movement of the probe can be improved. Otherwise, it may also be possible to improve the speed of movement of the probe by reducing the number of stages in a transmission focus or improve the speed of movement of the probe by fixing a reception focus and retrieving data. With such various methods, a time required for the pre-scanning can further be reduced.

In each of the embodiments, the example has been shown in which the air bubble that needs to be removed is determined by estimating the area of the air bubble and using the widths of the air bubble along the X- and Y-directions. However, the determination may also be made using another method. For example, it may also be possible to determine the gravity center of the air bubble and make a determination using the distance from the gravity center to the edge portion thereof.

Also, in the description of each of the embodiments, the C-mode image or the slice image is digitized for automatic determination of the air bubble that needs to be removed. However, it may also be possible to show the image to the operator and cause the operator to observe the image and determine the air bubble that needs to be removed. At this time, the image shown to the operator need not be one. It may also be possible to show a plurality of images in a plurality of slice planes and cause the operator to observe the plurality of images and make a determination.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-051905, filed on Mar. 14, 2013, which is hereby incorporated by reference herein in its entirety.

What is claimed is:

1. An object information acquiring apparatus comprising:
   a probe that transmits and receives the acoustic wave;
   a holding member disposed between the object and the probe to hold the object; and
   an air bubble detection unit that generates an image parallel to a surface between the object and the holding member on the basis of an intensity of the acoustic wave received by the probe and detects an air bubble present between the object and the holding member on the basis of the image.

2. The object information acquiring apparatus according to claim 1, wherein the air bubble detection unit further detects the air bubble on the basis of intensity of the acoustic wave received after a first time from the transmission by the probe, the first time being calculated on the basis of a time when the acoustic wave reaches a predetermined distance, wherein the predetermined distance is a sum of a distance from the probe to a plane in which the holding member is in contact with the object and a distance set on the basis of a size of the air bubble to be detected.

3. The object information acquiring apparatus according to claim 1, wherein the air bubble detection unit detects a region from the image where the intensity of the received acoustic wave is larger than a predetermined value, and determines that the air bubble is present in the region.

4. The object information acquiring apparatus according to claim 3, further comprising:
   a processing unit that generates internal information of the object related to an acoustic property on the basis of the acoustic wave received by the probe,
   wherein the air bubble detection unit notifies the processing unit that the internal information of the object cannot normally be acquired when a size of the detected air bubble exceeds a predetermined size.

5. The object information acquiring apparatus according to claim 4, wherein the air bubble detection unit notifies the processing unit that the internal information of the object cannot be acquired normally when an area of the detected air bubble is larger than a predetermined value.

6. The object information acquiring apparatus according to claim 4, wherein the air bubble detection unit notifies the processing unit that the internal information of the object cannot be acquired normally when a length of the shorter one of a maximum diameter of the detected air bubble along a first direction and a maximum diameter of the detected air bubble along a second direction orthogonal to the first direction is larger than a predetermined value.

7. The object information acquiring apparatus according to claim 1, wherein
   a second holding member is interposed between the holding member and the object, and
   the air bubble detection unit detects an air bubble present between the holding member and the second holding member and an air bubble present between the second holding member and the object.

8. The object information acquiring apparatus according to claim 1, wherein the air bubble detection unit generates the image on the basis of an intensity of the acoustic wave received after a first time from the transmission by the probe, the first time being calculated on the basis of a time when the acoustic wave reaches a predetermined distance.

9. An object information acquiring apparatus that irradiates an object with light, and receives and analyzes a photoacoustic wave generated in the object due to the light to acquire internal information of the object, comprising:
   a light irradiation unit that irradiates the object with the light;
   a probe that transmits and receives an acoustic wave, and receives the photoacoustic wave generated in the object due to the light;
   a holding member disposed between the object and the probe to hold the object; and
   an air bubble detection unit that generates an image parallel to a surface between the object and the holding member on the basis of an intensity of the acoustic wave received by the probe and detects an air bubble present between the object and the holding member on the basis of the image.

10. An image processing method, comprising:
    a generation step of generating an image parallel to a surface between an object and a holding member on the basis of an intensity of an acoustic wave received from the object by a probe, the probe transmitting and receiving the acoustic wave and the holding member being disposed between the object and the probe to hold the object; and
    an air bubble detection step of detecting an air bubble present between the object and the holding member on the basis of the image.

11. The image processing method according to claim 10, wherein the air bubble detection step further includes detecting the air bubble on the basis of intensity of the acoustic wave received after a first time from the transmission by the probe, the first time being calculated on the basis of a time when the acoustic wave reaches a predetermined distance, wherein the predetermined distance is a sum of a distance from the probe to a plane in which the holding member is in contact with the object and a distance set on the basis of a size of the air bubble to be detected.

12. The image processing method according to claim 10, wherein, in the air bubble detection step, an image representing the intensity of the received acoustic wave is generated, a region where the intensity of the received acoustic wave is larger than a predetermined value is detected from the image, and it is determined that the air bubble is present in the region.

13. The image processing method according to claim 12, further comprising:
    a processing step of generating internal information of the object related to an acoustic property on the basis of the acoustic wave received by the probe,
    wherein, in the air bubble detection step, the processing step is not executed when a size of the detected air bubble exceeds a predetermined size.

14. The image processing method according to claim 13, wherein, in the air bubble detection step, the processing step is not executed when an area of the detected air bubble is larger than a predetermined value.

15. The image processing method according to claim 13, wherein, in the air bubble detection step, the processing step is not executed when a length of the shorter one of a maximum diameter of the detected air bubble along a first direction and a maximum diameter of the detected air bubble along a second direction orthogonal to the first direction is larger than a predetermined value.

16. The image processing method according to claim 10, wherein
    a second holding member is interposed between the holding member and the object, and
    the air bubble detection step includes a step of detecting an air bubble present between the holding member and the second holding member and a step of detecting an air bubble present between the second holding member and the object.

17. An image processing method, comprising:
    generating an image parallel to a surface between an object and a probe on the basis of an intensity of an acoustic wave received from the object by the probe, the probe transmitting and receiving the acoustic wave; and
    detecting an air bubble between the object and the probe on the basis of the image.

18. The image processing method according to claim 17, further comprising issuing notification information about the detected air bubble.

19. An object information acquiring apparatus, comprising:
    a probe that transmits and receives an acoustic wave; and
    an air bubble detection unit that generates an image parallel to a surface between an object and the probe on the basis of an intensity of the acoustic wave received by the probe and detects an air bubble present between the object and the probe on the basis of the image.

20. An object information acquiring apparatus, comprising:
    a probe that transmits and receives an acoustic wave;
    an air bubble detection unit that generates an image on the basis of an intensity of the acoustic wave received by the probe and detects an air bubble present between the object and the probe on the basis of the image,
    wherein the air bubble detection unit detects a region from the image where the intensity of the received acoustic wave is larger than a predetermined value, and determines that the air bubble is present in the region.

* * * * *